United States Patent
Ueda et al.

(10) Patent No.: US 6,444,863 B2
(45) Date of Patent: *Sep. 3, 2002

(54) PROCESS FOR PRODUCING ALCOHOLS

(75) Inventors: Akio Ueda; Atsuhiro Adachi, both of Okayama (JP)

(73) Assignee: Mitsubishi Chemical Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,937

(22) Filed: May 20, 1999

(30) Foreign Application Priority Data

May 21, 1998 (JP) .......................................... 10-139511

(51) Int. Cl.[7] ........................... C07C 24/14; C07C 29/16
(52) U.S. Cl. ...................... 568/882; 568/881; 568/883
(58) Field of Search ................................. 568/882, 881, 568/454, 449, 883; 203/91; 549/503

(56) References Cited

U.S. PATENT DOCUMENTS

| 2,793,236 A | | 5/1957 | Habeshaw et al. | |
| 4,684,750 A | | 8/1987 | Kessen et al. | |
| 5,102,505 A | * | 4/1992 | Sorensen | 203/91 |

FOREIGN PATENT DOCUMENTS

| EP | 0094456 | * 11/1983 | ........... C07C/29/16 |
| FR | 2.011.758 | 3/1970 | |

* cited by examiner

*Primary Examiner*—Samuel Barts
*Assistant Examiner*—Elvis O. Price
(74) *Attorney, Agent, or Firm*—Oblon, Spivak, McClelland, Maier & Neustadt, P.C.

(57) ABSTRACT

A process for producing alcohols, to obtain a straight-chain alcohol having a carbon number of n (where n=3 to 6), a branched chain alcohol having a carbon number of n (where n=3 to 6) and a branched chain alcohol having a carbon number of 2n (where n=3 to 6) from a mixed aldehyde comprising a straight-chain aldehyde having a carbon number of n (where n=3 to 6) and a branched chain aldehyde having a carbon number of n (where n=3 to 6) in an optional proportion, which comprises supplying the mixed aldehyde to a distillation column, withdrawing from the bottom of the column an aldehyde rich in the straight-chain aldehyde, dimerizing the straight-chain aldehyde, followed by hydrogenation to obtain the branched chain alcohol having a carbon number of 2n, while obtaining, as a fraction from the top of the column, an aldehyde rich in the branched chain aldehyde and having a straight-chain aldehyde concentration in the fraction of at least 30 wt %, subjecting the fraction to hydrogenation, and purifying and separating the resulting straight-chain and branched chain mixed alcohol to obtain the straight-chain alcohol having a carbon number of n and the branched chain alcohol having a carbon number of n, respectively.

7 Claims, 1 Drawing Sheet

PROCESS FOR PRODUCING ALCOHOLS

Figure 1:
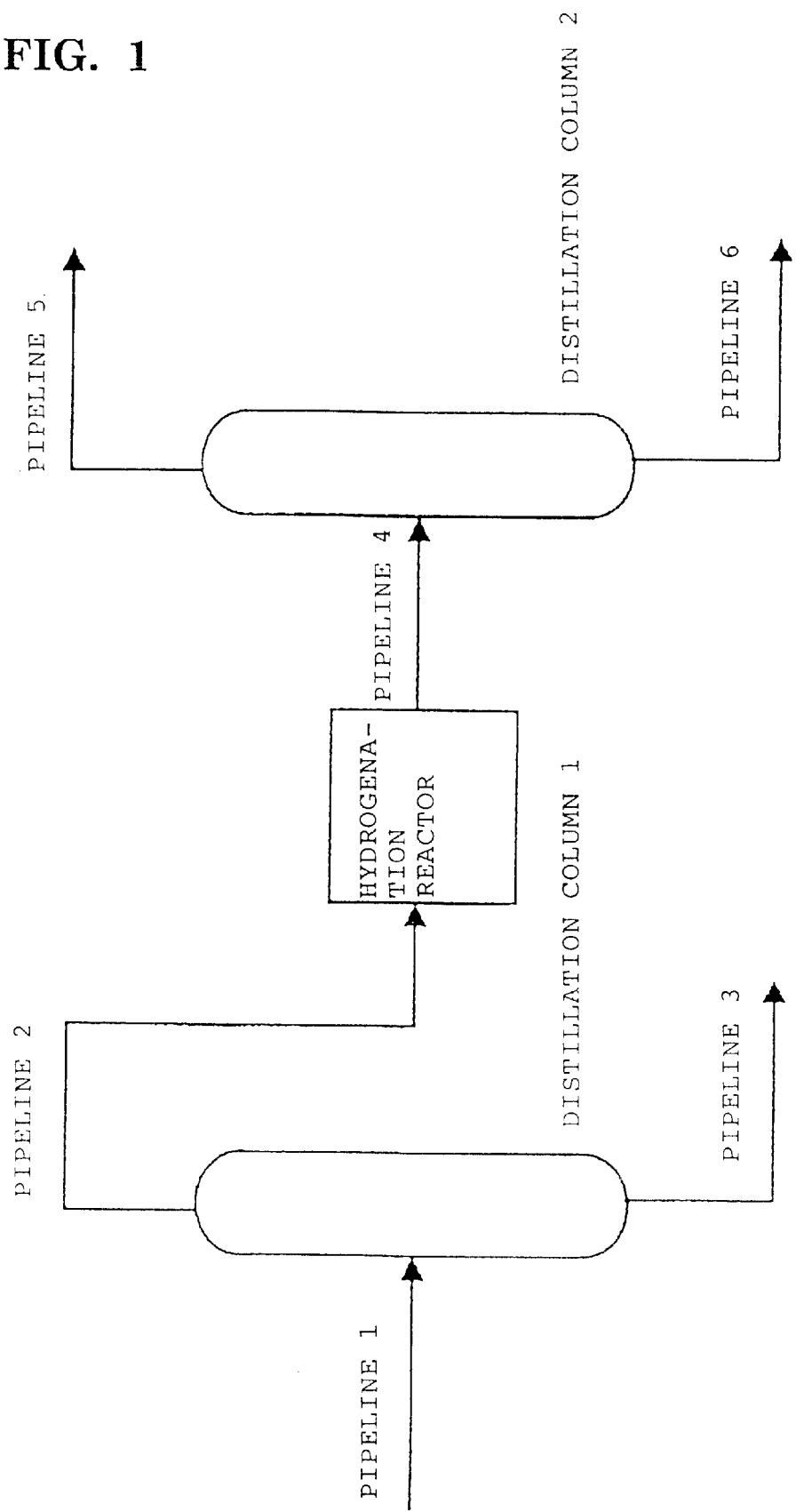

The present invention relates to a process for producing alcohols obtainable by hydrogenation of aldehydes. Particularly, it relates to a process for producing three types of alcohols i.e. a straight-chain alcohol and a branched chain alcohol each having a carbon number of n (where n=4 to 6) and a branched chain alcohol having a carbon number of 2n, in parallel, from a straight-chain and branched chain mixed aldehyde product having a carbon number of n, formed by hydroformylation of an olefin, whereby the energy cost and the installation cost can be reduced.

A process wherein a mixed aldehyde product is obtained by a so-called hydroformylation reaction i.e. by reacting an olefinic unsaturated compound with carbon monoxide and hydrogen in the presence of a complex catalyst having a Group VIII metal such as rhodium modified with a ligand containing phosphorus, the aldehyde product is separated by distillation into a straight-chain aldehyde and a branched chain aldehyde, the straight-chain aldehyde is subjected to aldol condensation to obtain a dimer of the straight-chain aldehyde, and the dimer is hydrogenated to obtain an alcohol having a carbon number of 2n, a process wherein the separated straight-chain aldehyde is directly hydrogenated to obtain a straight chain alcohol having a carbon number of n, and a process wherein the separated branched chain aldehyde is hydrogenated to obtain a branched chain alcohol having a carbon number of n, have been worldwidely industrially practiced. The above-mentioned mixed aldehyde product is one remaining after separating from the hydroformylation reaction zone the majority of an unreacted olefin, the solvent and the catalyst solution containing high boiling point by-products, and it contains, in addition to the straight-chain and branched chain aldehydes as the main components, a very small amount of dissolved gas (such as hydrogen, carbon monoxide, methane or carbon dioxide), a small amount of an unreacted olefin, paraffins and water, which are lighter than the main component aldehydes, an aldehyde having a carbon number smaller by one than the main component aldehydes, and a small amount of the solvent and high boiling point by-products, which have higher boiling points than the main component aldehydes.

Accordingly, a product obtained by separating the catalyst solution from the mixed aldehyde product is an isomer mixture comprising mainly a straight-chain aldehyde and a branched chain aldehyde. However, it is rare that this isomer mixture is used as it is, as a reaction material for the subsequent step, and it is commercially common to purify and separate the mixture into the straight-chain aldehyde and the branched chain aldehyde before use. As disclosed in U.S. Pat. No. 5,227,544, for example, in a case where 2-ethylhexanol having a carbon number of 2n is produced by aldol condensation of n-butyraldehyde, followed by hydrogenation, isobutyraldehyde contained as an impurity in said n-butyraldehyde is likely to finally change into isooctanol, thereby deteriorating the quality of 2-ethylhexanol product substantially. The above purification and separation is intended to prevent such deterioration of the product. On the other hand, with respect to isobutyraldehyde, for example, in a case where isobutyraldehyde is hydrogenated to obtain isobutanol, n-butyraldehyde contained as an impurity in said isobutyraldehyde, is likely to deteriorate the quality of the isobutanol product substantially, or substantially increase the cost for distillation for purification to maintain the quality. The above purification and separation is intended to avoid such drawbacks.

With respect to a conventional technique for separation of aldehyde isomers, for example, JP-A-4-273841 discloses a method wherein a mixed aldehyde product is distilled in a single distillation column to simultaneously obtain three types of independent product streams i.e. a purified branched chain aldehyde stream and two types of purified different straight chain aldehyde streams.

Further, U.S. Pat. No. 5,227,544 discloses a method wherein a small amount of water is added to a distillation column for aldehyde to hydrolyze an oligomer of isobutyraldehyde contained in crude butyraldehyde and to distill the entire amount as a monomer, thereby to produce 2-ethylhexanol of high purity.

Further, JP-A-8-169858 discloses a method of obtaining a straight-chain aldehyde from the bottom and a branched chain aldehyde from a position within theoretical plate numbers of from 5 to 15 plates from the top and above the feeding position, in the step for separating the mixed aldehyde product.

Further, JP-A-8-208554 discloses a method wherein a mixed aldehyde product is separated under a column top pressure of from 0.001 to 0.5 $kg/cm^2 G$ and a column bottom pressure of from 0.05 to 1.0 $kg/cm^2 G$, whereby n-butyraldehyde and isobutyraldehyde can be separated with a reduced energy cost.

The above-described methods are all concerned with a method for separating a mixed aldehyde. However, even by means of these methods, the aldehyde distillation column for separating the straight-chain aldehyde and the branched chain aldehyde, requires a large plate number and a large reflux amount, since the boiling points of aldehyde isomers to be separated, are very close to one another. Therefore, in order to obtain purified alcohols from such a mixed aldehyde economically, it is necessary to suppress the energy cost and the installation cost of the aldehyde distillation column.

Heretofore, industrially, improvement of the energy cost has been attempted by changing of the operation conditions or recovering waste heat from other heat generating step in the process. However, a method for more economically producing purified alcohols from a mixed aldehyde product, has been desired.

Accordingly, it is an object of the present invention to provide a process for economically producing alcohols from a mixed aldehyde product by reducing the energy cost and the installation cost of the aldehyde distillation column.

The present inventors have conducted an extensive study on the above subject and as a result, have found it possible to substantially reduce the energy cost such as a heat load and the theoretical plate number as compared with separating the mixed aldehyde in an aldehyde distillation column, by obtaining from the top of the aldehyde distillation column a fraction containing at least 30 wt %, preferably at least 50 wt %, of an aldehyde having a higher boiling point and separating a mixed alcohol obtained by hydrogenation of a mixed aldehyde obtained from the top of the column, into a straight-chain alcohol and a branched chain alcohol. The present invention has been accomplished on the basis of this discovery.

Namely, the present invention provides a process for producing alcohols, to obtain a straight-chain alcohol having a carbon number of n (where n=4 to 6), a branched chain alcohol having a carbon number of n (where n=4 to 6) and a branched chain alcohol having a carbon number of 2n (where n=4 to 6) from a mixed aldehyde comprising a straight-chain aldehyde having a carbon number of n (where n=4 to 6) and a branched chain aldehyde having a carbon number of n (where n=4 to 6) in an optional proportion, which comprises supplying the mixed aldehyde to a distillation column, withdrawing from the bottom of the column an aldehyde rich in the straight-chain aldehyde, dimerizing the straight-chain aldehyde, followed by hydrogenation to obtain the branched chain alcohol having a carbon number of 2n, while obtaining, as a fraction from the top of the column, an aldehyde rich in the branched chain aldehyde and having a straight-chain aldehyde concentration in the fraction of at least 30 wt %, preferably in the fraction of at least 50 wt %, subjecting the fraction to hydrogenation, and purifying and separating the resulting straight-chain and branched chain mixed alcohol to obtain the straight-chain alcohol having a carbon number of n and the branched chain alcohol having a carbon number of n, respectively.

Now, the present invention will be described in detail.

In the present invention, the mixed aldehyde to be separated and purified, is an aldehyde mixture comprising mainly a straight-chain aldehyde-having a carbon number of from 4 to 6 and a branched chain aldehyde having a carbon number of from 4 to 6. Such a mixed aldehyde is not particularly limited. However, it is preferred to employ, for example, the above-mentioned mixture obtained by hydroformylation of an olefin having a carbon number of from 3 to 5 such as propylene or butene.

An example of the method for producing a mixed aldehyde by a hydroformylation reaction will be described. The starting material propylene or butene may usually be employed without any special pre-treatment. However, a sulfur content or a halogen content known to be a catalyst poison, a diene, a triene, a peroxide, etc., may be removed by a conventional method such as adsorption, extraction, distillation, heat treatment or separation by a membrane, before use.

As the catalyst, a rhodium catalyst containing an organic phosphorus compound as a ligand, can be used. The organic phosphorus compound may, for example, be a trialkylphosphine such as tributylphosphine or trioctylphosphine, a triarylphosphine such as triphenylphosphine, tritolylphosphine or a triarylphosphine having hydrogen of a phenyl group substituted by e.g. a sulfonic group or a halogen, a tricycloalkylphosphine such as tricyclohexylphosphine, an alkylarylphosphine such as monobutyldiphenylphosphine or dipropylphenylphosphine, a cycloalkylarylphosphine, or an alkylcycloalkylphosphine. Further, a trialkylphosphite, a triarylphosphite such as triphenylphosphite or trinaphthylphosphite, which may have a substituent, or an alkylarylphosphite, may also be employed. Specifically, compounds disclosed in U.S. Pat. Nos. 3,415,906, 4,599, 206, 4,351,759, 4,748,261, 4,567,306, 5,235,113 and 5,227, 532 may be mentioned. However, in the present invention, the type of such an organic phosphorus compound is not limited.

Further, two or more among these organic phosphorus compounds may be used as a mixed ligand. Further, such an organic phosphorus compound may be used in admixture with a pentavalent organic phosphorus compound such as triphenylphosphine oxide.

As the rhodium source, in addition to a rhodium complex such as rhodium hydridocarbonyltris(triphenylphosphine) or rhodium acetoxybis(triphenylphosphine), an oxide such as rhodium acetylacetonate or rhodium acetate may, for example, be used. The rhodium source may directly be supplied to the hydroformylation reactor, but may preliminarily be treated with carbon monoxide and hydrogen in a solvent at a high temperature and pressure together with the ligand of an organic phosphorus compound outside the reactor, to prepare a catalyst solution. The solvent for the preparation of this catalyst solution is selected usually among the solvents for reaction as described hereinafter, but may not be the same as the solvent for reaction. With respect to the conditions for preparation of the catalyst, the rhodium concentration is usually from a few ppm to a few wt %, the ratio of the ligand of an organic phosphorus compound to rhodium is usually P/Rh=1 to 10,000 in a molar ratio, the temperature is from 60 to 200° C., the pressure is from atmospheric pressure to 200 kg/cm$^2$G, and the treating time is within a range of from a few minutes to a few tens hours.

The above treatment may be carried out by a batch system or a continuous system.

As the solvent for the hydroformylation reaction, the olefin itself may be used as the solvent, or a formed aldehyde or a high boiling point substance produced as a by-product by the reaction, may be used. Further, various solvents which are capable of dissolving the catalyst and which give no adverse effects to the reaction, may be employed, such as an aliphatic hydrocarbon such as hexane or octane, an aromatic hydrocarbon such as toluene or xylene, an alcohol such as butanol, 2-ethylhexanol, ethylene glycol or propylene glycol, an ether such as triglyme, an ester such as dioctyl phthalate, or water.

The hydroformylation reaction may be carried out usually under such conditions as a hydrogen partial pressure of from 0.1 to 200 kg/cm$^2$, a carbon monoxide partial pressure of from 0.1 to 200 kg/cm$^2$, a total pressure of a few kg/cm$^2$ to 300 kg/cm$^2$, a ratio of hydrogen partial pressure/carbon monoxide=0.1 to 10, a temperature of from 60 to 200° C., a rhodium concentration of from a few ppm to a few wt %, a molar ratio of P in the organic phosphorus compound ligand/Rh=1 to 10,000, and a reaction time of from a few minutes to a few tens hours.

The method for obtaining the mixed aldehyde from the reaction zone of hydroformylation which is carried out as described above, is not particularly limited and may, for example, be a method by gas stripping as disclosed in JP-A-52-125103 or a method by distillation as disclosed in JP-A-54-89974. By adopting any means, as a result, the majority of an unreacted olefin, the solvent and the catalyst solution containing high boiling point by-products, will be removed, and the components containing in the mixed aldehyde will be, other than the main component mixed aldehyde, a very small amount of dissolved gas (such as hydrogen, carbon monoxide, methane or carbon dioxide), a small amount of an unreacted olefin, paraffins and water, which are lighter than the aldehydes, a fraction lighter than the main component aldehydes, such as a low boiling point aldehyde having a carbon number smaller by one than the main component aldehydes, and a small amount of the solvent and high boiling point by-products, which have boiling points higher than the main component aldehydes.

BRIEF DESCRIPTIONS OF DRAWINGS

In the accompanying drawings,

FIG. 1 is a flowchart showing the general steps of the process of the present invention.

Referring to FIG. 1, an outline of the step of separating and purifying the mixed alcohol obtained by hydrogenation of the mixed aldehyde separated by distillation, according to the process of the present invention, will be described. Firstly, the mixed aldehyde is supplied from a pipeline 1 to a distillation column 1. From the mixed aldehyde supplied, a fraction having a straight-chain aldehyde content of at least 30 wt % is obtained from a pipeline 2, while the bottom wherein the main component is a straight-chain aldehyde, is obtained from a pipeline 3. The purity can be controlled by the theoretical plate number, the reflux ratio and the distillation ratio, but it is preferred to obtain the bottom having a straight-chain aldehyde content of at least 99.8 wt %.

The fraction containing at least 30 wt % of the straight-chain aldehyde, is supplied to a hydrogenation reactor via the pipeline 2 and subjected to a hydrogenation reaction to obtain a mixed alcohol comprising the straight-chain alcohol and the branched chain alcohol. This mixed alcohol is supplied to a distillation column 2 via a pipeline 4, whereupon the branched chain alcohol is obtained from a pipeline 5, and the straight-chain alcohol is obtained from a pipeline 6.

On the other hand, the bottom from the pipeline 3, which is rich in the straight-chain aldehyde, is subjected to an aldol condensation reaction by means of an alkali catalyst, and a diner aldehyde obtained by the reaction is further subjected to hydrogenation to obtain an alcohol having a carbon number of 2n. In FIG. 1, only a simple flow is illustrated to evaluate the energy and the installation required for separating the straight-chain and branched chain products. However, in a usual industrial operation, it is common to add a rectifying column to remove small amounts of low boiling point and high boiling point components contained in the alcohols.

The distillation column to be used in the present invention may be of any distillation system, so long as it is capable of directly separating the straight-chain aldehyde and the branched chain aldehyde, or the straight-chain alcohol and the branched chain alcohol.

The column top pressure of the distillation column is not particularly limited. However, it is preferably at least atmospheric pressure, since under reduced pressure, a loss of the aldehydes due to non-condensation is likely to result in the column top condenser employing cooling water of from about 20 to 30° C.

The temperature in the distillation column varies depending upon the carbon number of the aliphatic aldehyde, the column top pressure and the column bottom pressure determined by the type of the distillation column. However, it is preferably from about 62° C. to about 115° C. at the top of the column, and from about 76° C. to about 145° C. at the bottom of the column.

In the hydrogenation reaction, a conventional solid catalyst having a metal such as Ni, Cr or Cu supported on a carrier, may be used, and the hydrogenation can be carried out either in a gas phase or in a liquid phase. As the hydrogenation conditions, it is usual to employ a temperature of from 60 to 200° C. and a hydrogen pressure within a range of from 1 to 200 kg/cm$^2$G.

The aldol condensation reaction may be carried out in a liquid phase or in a gas phase. In a case where it is carried out in a liquid phase, an aqueous alkali catalyst solution such as an aqueous sodium hydroxide solution may be employed, and usually, the temperature is from 80 to 120° C., and the pressure is within a range of atmospheric pressure to 6 kg/cm$^2$G and at least the saturated pressure of the liquid at the set temperature.

Now, the present invention will be described in further detail with reference to Examples by process simulation calculation. However, it should be understood that the present invention is by no means restricted to such specific Examples.

COMPARATIVE EXAMPLE 1

A mixed aldehyde comprising n-butyraldehyde and isobutyraldehyde was supplied to a distillation column 1 via a pipeline 1 at 10 T/h. The straight-chain/branched chain ratio of the supplied liquid was 10, and the pressure for distillation was atmospheric pressure. In accordance with a conventional method, the straight-chain and the branched chain were separated in the distillation column 1, whereby n-butyraldehyde was obtained from a pipeline 3, and the isobutyraldehyde was obtained from a pipeline 2. The heat load for heating the distillation column was 2,830 Mcal/hr, and the theoretical plate number was 44.3 plates. The results are shown in Table 1.

COMPARATIVE EXAMPLE 2

A mixed aldehyde comprising n-butyraldehyde and isobutyraldehyde, was supplied to a distillation column 1 from a pipeline 1 at 10 T/h. The straight-chain/branched chain ratio in the supplied liquid was 70, and the pressure for distillation was atmospheric pressure. In accordance with a conventional method, the mixed aldehyde was separated by the distillation column 1, whereby n-butyraldehyde was obtained from a pipeline 3, and isobutyraldehyde was obtained from a pipeline 2. The heat load for heating the distillation column was 7150 Mcal/hr, and the theoretical plate number was 44.0 plates. The results are shown in Table 1.

COMPARATIVE EXAMPLES 3 to 5

A mixed aldehyde comprising n-butyraldehyde and isobutyraldehyde, was supplied to a distillation column 1 from a pipeline 1 at 10 T/h. The straight-chain/branched chain ratio in the supplied liquid was 70 or 10, as identified in Table 1, and the pressure for distillation was atmospheric pressure. From the distillation column 1, a fraction containing from 5 to 20 wt % of n-butyraldehyde was obtained from a pipeline 2. This fraction was subjected to a hydrogenation reaction in a hydrogenation reactor to obtain a mixed alcohol comprising n-butyl alcohol and isobutyl alcohol from a pipeline 4. The mixed alcohol was supplied to a distillation column 2, whereupon isobutyl alcohol was obtained from a pipeline 5, and n-butyl alcohol was obtained from a pipeline 6. The results are shown in Table 1.

EXAMPLES 1 to 4

A mixed aldehyde comprising n-butyraldehyde and isobutyraldehyde was supplied to a distillation column 1 from a pipeline 1 at 10 T/h. The straight chain/branched chain ratio in the supplied liquid was 70 or 10 as identified in Table 1, and the pressure for distillation was atmospheric pressure. From the distillation column 1, a fraction containing from 40 to 97 wt % of n-butyraldehyde was obtained from a pipeline 2. This fraction was subjected to a hydrogenation reaction in a hydrogenation reactor, to obtain a mixed alcohol comprising n-butyl alcohol and isobutyl alcohol from a pipeline 4. The mixed alcohol was supplied to a distillation column 2, whereupon isobutyl alcohol was obtained from a pipeline 5, and n-butyl alcohol was obtained from a pipeline 6. The results are shown in Table 1.

From the foregoing Comparative Examples and Examples, it is evident that as a method for obtaining straight-chain and branched chain alcohols in high purity from a mixed aldehyde composed essentially of isomer aldehydes, rather than precisely separating the mixed aldehyde by a distillation column before conversion to alcohols, it is better that in a first distillation column, a mixed aldehyde containing at least 30 wt % of a straight-chain aldehyde, is distilled, and it is subjected to a hydrogenation reaction to obtain a mixed alcohol, and the mixed alcohol is subjected to distillation and separation in a second distillation column, whereby the energy efficiency totaling the two columns is good, and the total theoretical plate number can be made small. Further, the bottom from the first distillation column is rich in the straight-chain aldehyde and usually contains at least 99.8 wt % thereof, and by subjecting the bottom to aldol condensation, followed by hydrogenation, it is possible to produce the alcohol having a carbon number of 2n with good purity in parallel.

TABLE 1

|  | Comparative Example 1 | Comparative Example 4 | Comparative Example 5 | Example 2 |
|---|---|---|---|---|
| Distillation column 1 |  |  |  |  |
| Supplied NBD (kg/hr) | 9090.8 | 9090.8 | 9090.8 | 9090.8 |
| Supplied IBD (kg/hr) | 909.2 | 909.2 | 909.2 | 909.2 |
| NBD/IBD | 10 | 10 | 10 | 10 |
| Distilled NBD (kg/hr) | 0.0897 (0.01 wt %) | 46.9 (5 wt %) | 222.9 (20 wt %) | 5106.9 (85 wt %) |
| Distilled IBD (kg/hr) | 891.0 | 891.1 | 891.4 | 901.2 |
| Bottom NBD (kg/hr) | 9090.7 (99.8 wt %) | 9043.9 (99.8 wt %) | 8867.9 (99.8 wt %) | 3983.9 (99.8 wt %) |
| Bottom IBD (kg/hr) | 18.2 | 18.1 | 17.8 | 8.0 |
| Theoretical plate number | 44.3 | 26.1 | 21.7 | 12.8 |
| Reboiler heat load (Mcal/hr) | 2830 | 2800 | 2670 | 1170 |
| Distillation column 2 |  |  |  |  |
| Supplied NBA (kg/hr) |  | 48.2 | 229.1 | 5248.8 |
| Supplied IBA (kg/hr) |  | 915.9 | 916.2 | 926.2 |
| Distilled NBA (kg/hr) |  | 2.756 | 2.753 | 2.73 |
| Distilled IBA (kg/hr) |  | 915.8 (99.7 wt %) | 915.7 (99.7 wt %) | 915.5 (99.7 wt %) |
| Bottom NBA (kg/hr) |  | 45.4 (99.8 wt %) | 226.3 (99.8 wt %) | 5246.1 (99.8 wt %) |
| Bottom IBA (kg/hr) |  | 0.0966 | 0.459 | 10.7 |
| Theoretical plate number |  | 18.1 | 18.1 | 18.1 |
| Reboiler heat load (Mcal/hr) |  | 370 | 430 | 1390 |
| Total of two columns |  |  |  |  |
| Theoretical plate number | 44.3 | 44.2 | 39.8 | 30.9 |
| Reboiler heat load (Mcal/hr) | 2830 | 3270 | 3100 | 2560 |

|  | Comparative Example 2 | Comparative Example 3 | Example 1 | Example 3 | Example 4 |
|---|---|---|---|---|---|
| Distillation column 1 |  |  |  |  |  |
| Supplied NBD (kg/hr) | 9859.2 | 9859.2 | 9859.2 | 9859.2 | 9859.2 |
| Supplied IBD (kg/hr) | 140.8 | 140.8 | 140.8 | 140.8 | 140.8 |
| NBD/IBD | 70 | 70 | 70 | 70 | 70 |
| Distilled NBD (kg/hr) | 0.0127 (0.001 wt %) | 6.37 (5 wt %) | 182.1 (50 wt %) | 4184.4 (97 wt %) | 121.1 (40 wt %) |
| Distilled IBD (kg/hr) | 121.1 | 121.1 | 121.4 | 129.4 | 80.8 |
| Bottom NBD (kg/hr) | 9859.2 (99.8 wt %) | 9852.8 (99.8 wt %) | 9677.1 (99.8 wt %) | 5674.8 (99.8 wt %) | 9778.4 (99.8 wt %) |
| Bottom IBD (kg/hr) | 19.7 | 19.7 | 19.4 | 11.4 | 19.6 |
| Theoretical plate number | 44.0 | 26.1 | 16.5 | 7.8 | 18.9 |
| Reboiler heat load (Mcal/hr) | 7150 | 2470 | 2200 | 1270 | 2350 |

TABLE 1-continued

| Distillation column 2 | | | | | |
| --- | --- | --- | --- | --- | --- |
| Supplied NBA (kg/hr) | | 6.55 | 187.2 | 4300.9 | 83.1 |
| Supplied IBA (kg/hr) | | 124.5 | 124.8 | 133 | 124.5 |
| Distilled NBA (kg/hr) | | 0.375 | 0.374 | 0.36 | 0.375 |
| Distilled IBA (kg/hr) | | 124.5 (99.7 wt %) | 124.4 (99.7 wt %) | 124.4 (99.7 wt %) | 124.3 (99.7 wt %) |
| Bottom NBA (kg/hr) | | 6.175 (99.8 wt %) | 186.8 (99.8 wt %) | 4300.5 (99.8 wt %) | 82.72 (99.8 wt %) |
| Bottom IBA (kg/hr) | | 0.0131 | 0.375 | 8.6 | 0.165 |
| Theoretical plate number | | 18.1 | 18.2 | 18.2 | 18.2 |
| Reboiler heat load (Mcal/hr) | | 50 | 90 | 800 | 70 |
| Total of two columns | | | | | |
| Theoretical plate number | 44.0 | 44.2 | 34.7 | 26.0 | 37.1 |
| Reboiler heat load (Mcal/hr) | 7150 | 2520 | 2290 | 2070 | 2420 |

NBD: n-Butyraldehyde, IBD: Isobutyraldehyde, NBA: n-Butyl alcohol, IBA: Isobutyl alcohol In accordance with the present invention, the mixed aldehyde is treated in the first distillation column to obtain a fraction containing the straight-chain aldehyde and the branched chain aldehyde in a specific ratio, followed by hydrogenation to obtain a mixed alcohol, which is separated into the respective isomer alcohols, while the bottom from the first distillation column is subjected to aldol condensation, followed by hydrogenation to obtain the alcohol having a carbon number of 2n, whereby, while a large energy used to be consumed for separating the aldehyde isomers, both the theoretical plate number and the reboiler heat load can be substantially reduced as compared with the conventional method, and the three types of alcohols can be produced in parallel. Thus, the value of the present invention for industrial application is very high.

What is claimed is:

1. A process for producing alcohols, to obtain a straight-chain alcohol having a carbon number of n (where n=4 to 5), a branched-chain alcohol having a carbon number of n (where n=4 to 5) and a branched-chain alcohol having a carbon number of 2n (where n=4 to 5) from a mixed aldehyde comprising a straight-chain aldehyde having a carbon number of n (where n=4 to 5) and a branched-chain aldehyde having a carbon number of n (where n=4 to 5) in an optional proportion, which comprises supplying the mixed aldehyde to a distillation column, withdrawing from the bottom of the column an aldehyde rich in the straight-chain aldehyde, dimerizing the straight-chain aldehyde, followed by hydrogenation to obtain the branched chain alcohol having a carbon number of 2n, while obtaining, as a fraction from the top of the column, an aldehyde rich in the branched-chain aldehyde and having a straight-chain aldehyde concentration in the fraction of at least 30 wt %, subjecting the fraction to hydrogenation, and purifying and separating the resulting straight-chain and branched-chain mixed alcohol to obtain the straight-chain alcohol having a carbon number of n and the branched chain alcohol having a carbon number of n, respectively, the mixed aldehyde as the starting material being one obtained by hydroformylation of butene and/or propylene.

2. The process for producing alcohols according to claim 1, wherein the straight-chain alcohol concentration in the fraction from the top of the column is at least 50 wt %.

3. The process for producing alcohols according to claim 1, wherein the carbon number n=4.

4. The process for producing alcohols according to claim 1, wherein a catalyst for the hydroformylation is a rhodium catalyst containing an organic phosphorus compound as a ligand.

5. The process for producing alcohols according to claim 1, wherein the straight-chain aldehyde content in the aldehyde withdrawn from the bottom of the column is at least 99.8 wt %.

6. The process for producing alcohols according to claim 1, wherein the straight-chain and branched chain mixed alcohol obtained by hydrogenation of the fraction from the top of the column, is purified and separated by distillation to obtain the straight-chain alcohol having a carbon number of n and the branched chain alcohol having a carbon number of n, respectively.

7. The process for producing alcohols according to claim 1, wherein the column top pressure of the distillation column for separating the straight-chain aldehyde and the branched chain aldehyde, and the straight-chain alcohol and the branched chain alcohol, is at least atmospheric pressure.

* * * * *